United States Patent [19]
Falkowski et al.

[11] Patent Number: 5,801,010
[45] Date of Patent: Sep. 1, 1998

[54] SELF-CONTAINED BIOLOGICAL INDICATOR FOR NON TRADITIONAL STERILIZATION METHODS

[75] Inventors: Jerry Falkowski, Cary; Giridhar Shamsunder, Raleigh; Steven J. Risner, Apex; Pamela M. Lyons, Raleigh, all of N.C.

[73] Assignee: Surigot, Inc., Research Triangle Park, N.C.

[21] Appl. No.: 818,944

[22] Filed: Mar. 17, 1997

[51] Int. Cl.$^6$ .................................................. C12M 3/00
[52] U.S. Cl. .............. 435/31; 435/34; 435/287.4; 435/287.6; 435/808
[58] Field of Search ............... 435/287.4, 287.6, 435/808, 31, 34

[56] References Cited

U.S. PATENT DOCUMENTS

| | | | |
|---|---|---|---|
| 4,416,984 | 11/1983 | Wheeler et al. | 435/31 |
| 4,528,268 | 7/1985 | Andersen et al. | 435/31 |
| 4,829,001 | 5/1989 | Mencke et al. | 435/264 |
| 5,223,401 | 6/1993 | Foltz et al. . | |
| 5,405,580 | 4/1995 | Palmer . | |
| 5,500,184 | 3/1996 | Palmer . | |
| 5,552,320 | 9/1996 | Smith . | |

*Primary Examiner*—David Redding
*Attorney, Agent, or Firm*—Mills Law Firm PLLC

[57] ABSTRACT

A self-contained biological indicator for evaluating the efficacy of sterilization processes utilizing hydrogen peroxide and hydrogen peroxide/peracetic acid plasma and vapor as the sterilant is disclosed. The self-contained biological indicator includes a translucent, vapor-permeable, container including a source of dormant microorganisms, a sealed ampule containing a culture medium that is capable of promoting the growth of surviving microorganisms, a neutralizing tablet that is capable of decomposing hydrogen peroxide sterilant, and an actuating mechanism that permits mixture of the source of microorganisms, culture medium and the hydrogen peroxide neutralizing tablet to be brought into contact from the exterior of the indicator. In one embodiment the self-contained biological indicator is comprised of a plurality of generally cylindrical, telescoping vials being operable from an unsealed, sterilization test configuration to a sealed and activated configuration for incubation. In the sterilization test configuration the integrity of the enclosure is interrupted by a plurality of openings which permit the flow of sterilant vapor into the indicator during a sterilization cycle. After exposure to the sterilization cycle is complete the indicator is operable to a sealed configuration in which the gas permeable openings are blocked by the telescoping movement of the container vials. After the indicator has been exposed to a sterilization cycle and placed in the sealed condition the deformable container may be actuated by finger pressure to bring the microorganism source, culture medium, and the hydrogen peroxide decomposing tablet into contact.

13 Claims, 11 Drawing Sheets

SELF-CONTAINED BIOLOGICAL INDICATOR FOR NON TRADITIONAL STERILIZATION METHODS

BACKGROUND OF INVENTION

1. Field of Invention

This invention relates to biological indicators for evaluating sterilization of processes and, more particularly, to an improved self-contained biological indicator for a hydrogen peroxide sterilizer.

Sterilization is a process conducted in a specially designed chamber or sterilizer that results in a complete eradication of all viable micro-organisms. Sterilization techniques have evolved over time from the traditional methods employing saturated steam at elevated temperature and ethylene oxide gases to more modern techniques such as those employing liquid, vapor, and plasma. The effectiveness of the applied sterilization process must be evaluated regardless of the technique utilized especially when sterilization of instruments and devices invasive to the human body are concerned.

So-called biological indicators are devices that are used to test the efficacy of sterilization chambers such as those employed in hospitals for sterilizing medical and surgical instruments. Typically the biological indicator includes a source of microorganisms, a culture medium, and a visible detector to indicate the presence or absence of viable microorganisms.

In practice, the source of microorganisms, typically an absorbent paper strip that has been impregnated with a pre-determined concentration of live microorganisms, is subjected to the sterilization process. Thereafter, the microorganism impregnated strip is placed in a sterile culture medium and incubated for a predetermined time at an appropriate temperature. At the end of the incubation period, the detector is used to determine whether any microorganisms survived the sterilization process.

One of the most convenient and practical forms of biological indicators being used today is a self-contained biological indicator (SCBI) which contains all of the necessary elements of the biological indicator-microorganisms, culture medium, and a detector.

One of the most critical features of the (SCBI) is that upon activation any possibility of exogenous contamination is reduced to a minimum thereby reducing a false positive reading to a minimal statistical probability. However, the same feature can have an adverse effect if residue of the hydrogen peroxide sterilizing agent is trapped inside of the (SCBI) micro-environment. This sterilizing agent residue can have an inhibitory effect on microorganism growth and give a false negative test result resulting in the presence of contaminated items among those items sterilized. The sterilizing agent residue problem occurs in both hydrogen peroxide and hydrogen peroxide/peracetic acid sterilizers as well as in hydrogen peroxide vapor sterilizers in the form of plasma, vapor and condensate.

During the sterilization cycle, hydrogen peroxide can be absorbed by the paper strip or sporedot that contains the viable microorganisms. At the end of the sterilization cycle viable microorganisms may remain indicating the sterilization technique was ineffective.

However, the surviving microorganisms can be killed by the subsequent release of the absorbed hydrogen peroxide sterilant. Thus, when the (SCBI) is activated by adding the growth promoting media there would be no growth of microorganisms giving a false negative result.

The problem of neutralizing hydrogen peroxide and other oxidant residues has been addressed in the prior art. For example, U.S. Pat. No. 4,829,001 discloses a method for disinfecting a medical device comprising steps of immersing the device in hydrogen peroxide solution for a time sufficient to disinfect the device and decomposing any residual hydrogen peroxide by use of a catalytically effective amount of catalase or peroxidase mobilized on a composite article. Enzymatic decomposition leads to liberation of oxygen and creation of water or in the case of peracetic acid, acetic acid which can also be neutralized.

Thus, if viable microorganisms survive the sterilization procedure they will thrive and reproduce in a growth promoting medium containing catalase when incubated and will be detected.

However, the commercial (SCBI's) of the prior art have not achieved optimum accuracy and reliability due to the manner in which the neutralizing enzyme, catalase, is delivered to the growth promoting medium after the sterilization process. The composition of the tablets or beads of catalase must be such that the catalase carrier does not inhibit any stage of germination or growth of the organisms surviving the sterilization process and must at the same time provide microorganisms with a high number of microsurfaces to stimulate exponential growth by adherence thereto.

The catalase tablet or bead must not be metabolized by the microorganism and must not change the liquid consistency and composition of the included growth promoting medium nor provide additional pH buffering ability. Further catalase tablets or beads must readily disintegrate upon contact with the culture medium releasing catalase into the immediate microenvironment of the (SCBI) for the purpose of inactivating the hydrogen peroxide residue of the sterilization process.

Many such commercially available (SCBI's) can be utilized for monitoring plasma/vapor hydrogen peroxide and hydrogen peroxide/peracetic acid sterilization cycles. However, for the reasons indicated hereinabove, they may potentially indicate false completion of the sterilization cycle.

Thus, the present invention has been developed to provide an improved (SCBI) to avoid false sterilization process efficacy indications.

2. Description of Related Art

U.S. Pat. No. 5,552,320 to Daniel F. Smith discloses a self-contained biological indicator including an outer container that is translucent and liquid impermeable. The container is normally closed by a vapor-permeable, microorganism-impermeable closure and contains a source of viable microorganisms, a culture medium, a composition that decomposes hydrogen peroxide, and a detector that undergoes a visible change in response to growth of the microorganisms.

U.S. Pat. Nos. 5,405,580 and 5,500,184 to Stephen G. Palmer disclose biological indicators for determining the efficacy of a sterilization cycle using hydrogen peroxide vapor at sub atmospheric conditions. The biological indicators include a vial formed of a substance which resists retention of residual sterilant while also maintaining vial clarity.

U.S. Pat. No. 5,223,401 to William E. Foltz, et al. discloses a unitary sterility indicator and method for its use, the indicator comprising an outer container having liquid impermeable and gas non-absorptive walls and having a gas-transmissive bacteria impermeable opening therein.

Finally, U.S. Pat. No. 4,829,001 to Arlene J. Mencke discloses a method for disinfecting a medical device comprising the steps of immersing a medical device in a hydrogen peroxide solution for a time sufficient to disinfect the device, and decomposing any residual hydrogen peroxide by use of catalytically effective amount of catalase or peroxidase immobilized on a composite article.

SUMMARY OF INVENTION

After much research and study into the above mentioned problems, the present invention has been developed to provide an improved self-contained biological indicator (hereinafter "SCBI") for indicating the efficacy of sterilization processes implementing hydrogen peroxide and hydrogen peroxide/peracetic acid plasma and vapor as a means of effective terminal sterilization.

In accordance with the present invention, a (SCBI) for monitoring sterilization processes using hydrogen peroxide and hydrogen peroxide/peracetic acid in the form of vapor or plasma as sterilizing agents and for the delivery of enzymatic neutralizer of oxidant process residue includes:

a) translucent, liquid/gas impermeable containers or vials having openings for sterilizing agent penetration, b) a cap attachable to the container or vial which during (SCBI) activation creates a liquid-proof microenvironment inside of the (SCBI), c) a glass ampule containing growth promoting media equipped with microorganism metabolites level visual detector, d) a means of viable microorganism dormant delivery to the (SCBI) such as an absorbent paper strip that has been impregnated with a predetermined concentration of microorganisms, and e) a means of residual sterilizing agent decomposition/neutralization such as a catalytically effective amount of catalase in the form of a bead or tablet.

In view of the above, it is an object of the present invention to provide an improved (SCBI) which will provide an accurate indication of the efficacy of sterilization processes utilizing hydrogen peroxide and hydrogen peroxide/peracetic acid plasma and vapor as a means of sterilization.

Another object of the present invention is to provide an improved liquid/gas impermeable container for a (SCBI) formed from a plurality of telescoping vial components which are assembled to form a sealed enclosure inaccessible to external environmental factors.

Another object of the present invention is to provide an improved (SCBI) wherein activation thereof is performed by compressing the deformable walls of the container to mix the growth promoting media, the dormant microorganisms, and the sterilizing agent neutralizer without exposure to external environmental factors.

Another object of the present invention is to provide an improved (SCBI) that increases the industrial shelf life of such devices due to the chemical composition of the hydrogen peroxide neutralizing tablet contained therein.

Other objects and advantages of the present invention will become apparent and obvious from a study of the following description and the accompanying drawings which are merely illustrative of such invention.

DETAILED DESCRIPTION OF THE PREFERRED EMBODIMENT

Figure 1:
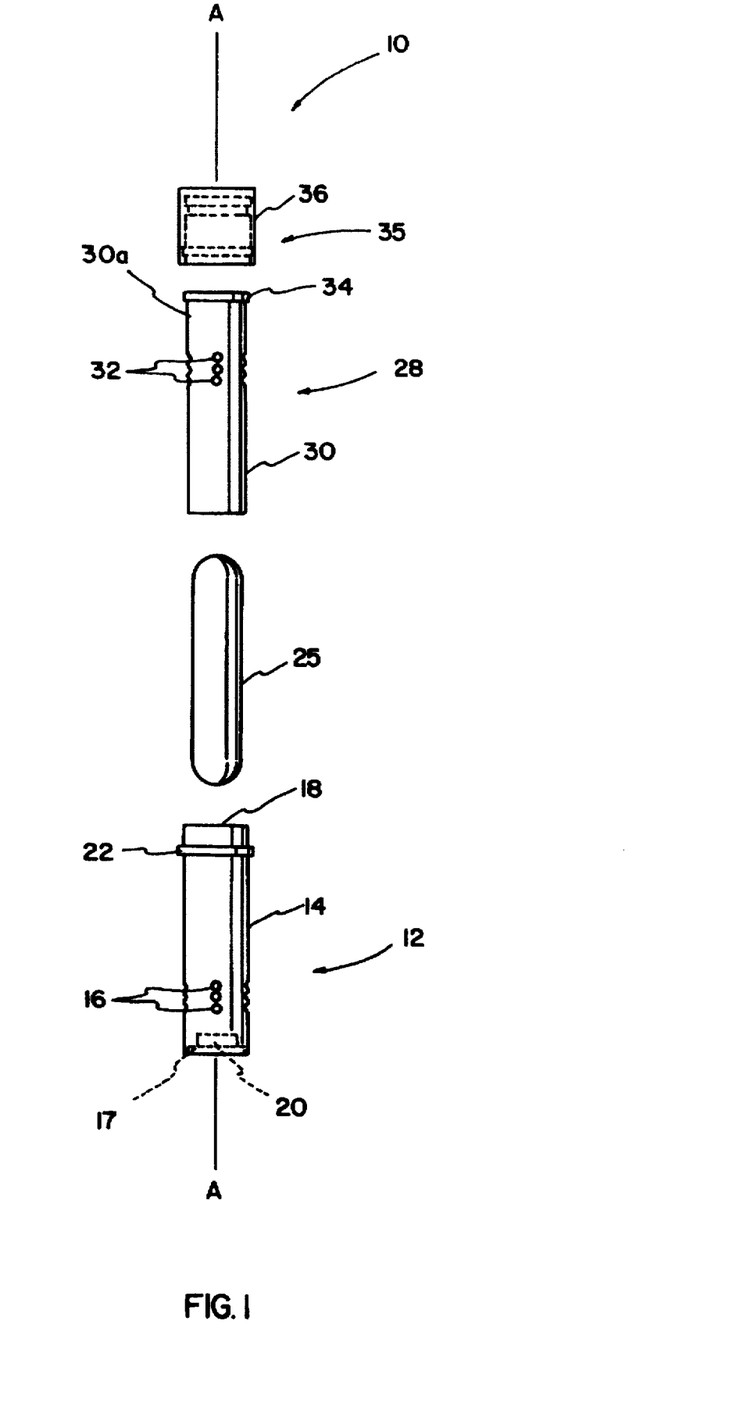
FIG. 1 is an exploded elevational view of the improved (SCBI) of the present invention showing the components thereof.

With further reference to the drawings there is shown therein an exploded view of the improved (SCBI) of the present invention indicated generally at 10 and illustrated in FIG. 1. The improved (SCBI) of the present invention includes a translucent outer vial, indicated generally at 12, having gas/liquid impermeable walls 14 with a plurality of openings 16 formed therein for permitting sterilizing agent penetration. The outer vial 12 includes a closed end 17 and an open end 18 into which a hydrogen peroxide neutralizing tablet 20 containing catalase has been deposited.

Figure 2:
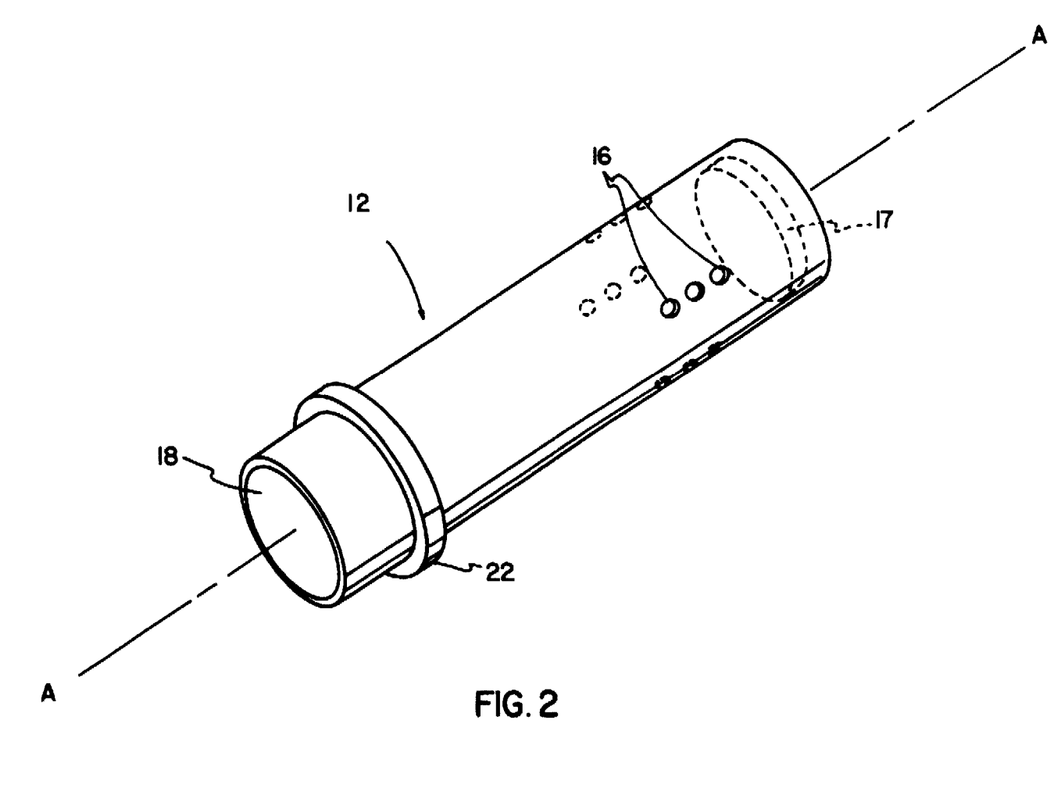
FIG. 2 is a perspective view of a preferred embodiment of the outer vial of the (SCBI) showing the details thereof.

Outer container 12 further includes a locking flange 22 that is integrally formed with the wall 14 of the outer vial 12 in generally perpendicular relation to a longitudinal axis A thereof as more clearly shown in FIG. 2.

In the preferred embodiment the outer vial 12 is fabricated from a flexible, translucent plastic material such as polypropylene or other suitable translucent material.

In the present specification and claims, the term "translucent" is defined as that quality of the vial walls that permits visible changes to be detected from the exterior. Thus, for example, transparent walls would clearly be included and the present vial is also substantially transparent permitting more precise determination of the change pointing to non-sterile conditions.

Figure 3:
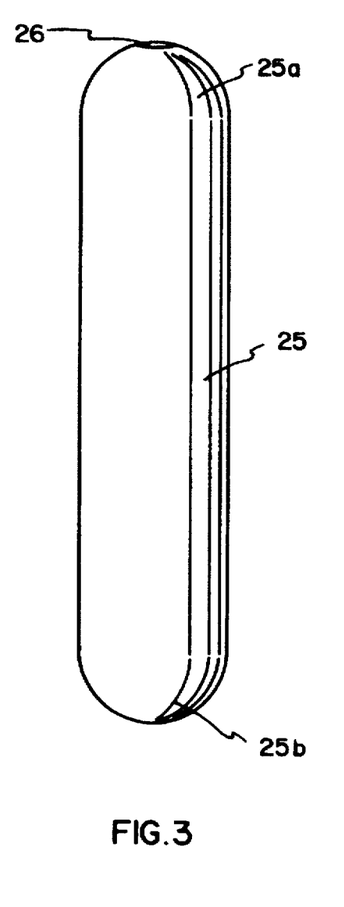
FIG. 3 is an elevational view of a frangible ampule of the present invention for containing a culture medium.

The outer vial 12 is configured and dimensioned to slidingly receive an ampule 25 containing a growth promoting media (not illustrated) as shown in FIG. 3.

Since such growth promoting media are well known to those skilled in the art, further detailed discussion of the same is not deemed necessary.

In the preferred embodiment ampule 25 is a sealed enclosure formed from a frangible material such as glass or other suitable material to permit ampule 25 to be opened by crushing with finger pressure without breaking the deformable walls 14 of the outer vial 12 during activation of the (SCBI) as is described hereinafter in further detail.

In FIG. 3 it can be seen that the ampule 25 includes generally hemispherical ends 25a and 25b.

Since various changes in the above construction could be made to accommodate different shapes of ampules without departing from the scope of the invention, matter contained in the accompanying drawing figures shall be interpreted as illustrative and not restrictive in any since.

In the preferred embodiment an absorbent paper strip or sporedot 26 inoculated with a predetermined number of dormant microorganisms is disposed at one end of ampule 25 as shown in FIG. 3.

Since such paper strips inoculated with microorganisms are well known to those skilled in the art, further detailed discussion of the same is not deemed necessary.

Figure 4:
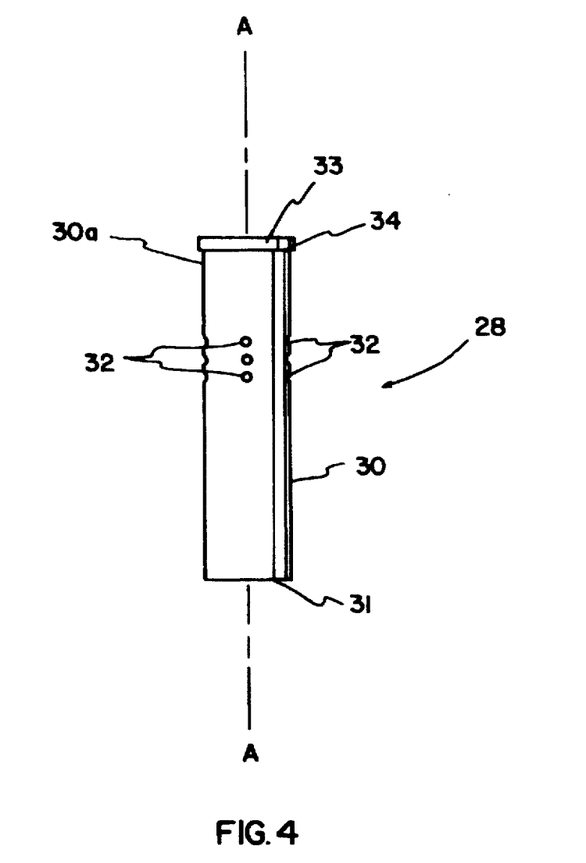
FIG. 4 is an elevational view of a preferred embodiment of the inner vial of the (SCBI) showing the details thereof.

The (SCBI) includes an inner vial, indicated generally at 28, also having translucent, gas/liquid impermeable walls and having an open end 31 and a closed end 33 thereof as shown in FIG. 4.

The integrity of the wall 30 of inner vial 28 is interrupted by the formation of a plurality of openings 32 which permit the flow of sterilizing agent to permeate to the inner surfaces of the vial 28 during sterilization.

A distal end 30a of inner vial 28 is provided with a locking rim 34 being integrally formed thereon and disposed in generally perpendicular relation to a longitudinal axis A of the inner vial 28.

The inner vial 28 is configured and dimensioned for telescoping engagement within outer vial 12 prior to activation of the (SCBI) as described hereinafter in further detail.

Figure 5:
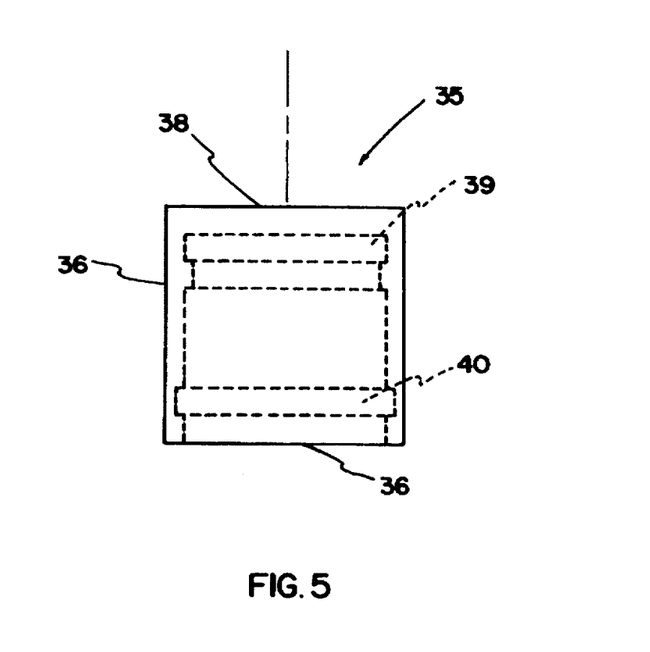
FIG. 5 is an alevational view of the locking cap of the (SCBI) showing the details thereof.

The (SCBI) of the present invention is also provided with a locking cap, indicated generally at 35 as illustrated in FIG. 5. Cap 35 includes generally cylindrical, gas/liquid impermeable walls 36 having an open end 37 and a closed end 38.

Cap 35 includes a pair of generally parallel, circumferential grooves 39 and 40 being integrally formed about the inside diameter thereof as clearly shown in FIG. 5.

Grooves 39 and 40 are configured and dimensioned so as to engage locking rim 34 of inner vial 28 and the locking flange 22 of outer vial 12 when the (SCBI) is sealed for incubation as described hereinafter in further detail.

Figure 6A:
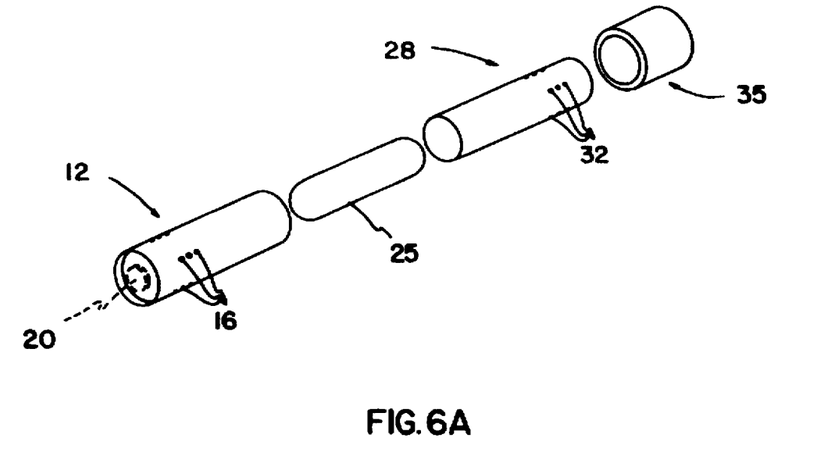
FIG. 6A is an exploded perspective view of the components of the (SCBI) to be assembled.
Figure 6B:
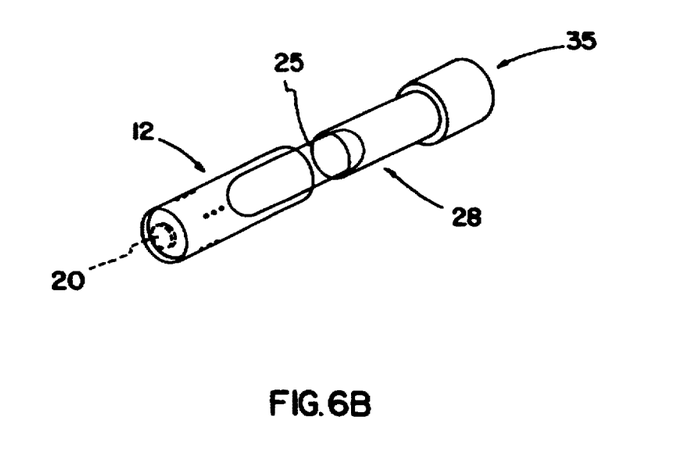
FIG. 6B is a partially exploded perspective view of the (SCBI) being assembled.
Figure 6C:
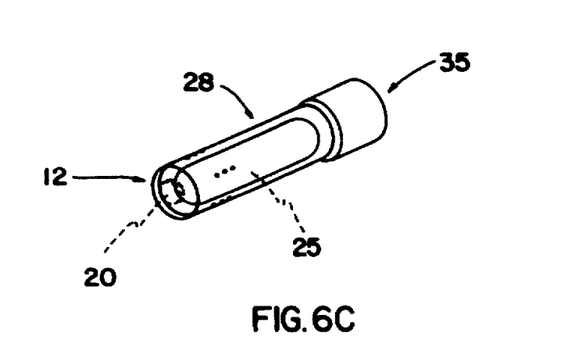
FIG. 6C is a perspective view of the (SCBI) in the unsealed sterilization test configuration.

Prior to placing it within the chamber of the sterilizer along with the objects to be sterilized, the improved (SCBI) is assembled to the unsealed sterilization test position as shown in FIGS. 6A–6C.

During the sterilization cycle the sterilant vapor permeates through the openings 16 and 32 to the interior surfaces of outer vial 12 and inner vial 28 respectively where it acts on the microorganism inoculated strip 26 together with the contents and interior surfaces of the (SCBI).

Figure 6D:
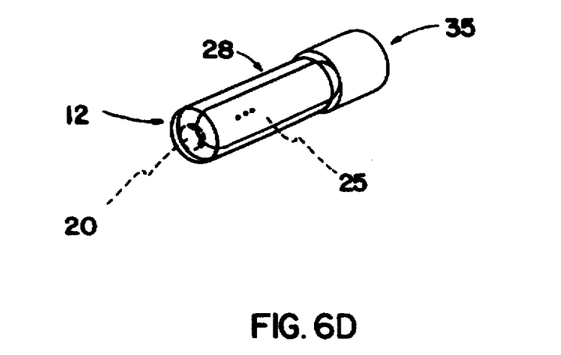
FIG. 6D is a perspective view of the (SCBI) in the sealed incubation configuration.

After being subjected to a sterilization cycle the inner vial 28 is inserted firmly into the outer vial 12 to the sealed incubation condition shown in FIG. 6D.

Thereafter, the sterilized cap 35 is installed thereon so as to engage the locking rim 34 and the locking flange 22 within groves 39 and 40 to form a waterproof closure inaccessible to external environmental factors.

In normal use the (SCBI) is activated by compressing the deformable walls of the inner and outer vials 12 and 28 respectively to break the ampule 25 containing the growth promoting media, which comes into contact with the neutralizer tablet 20.

The chemical composition of tablet 20 could be any number of compositions known in the prior art as being suitable for decomposing hydrogen peroxide including catalase, peroxidase and other peroxide neutralizing catalysts. The composition of tablets or beads 20 must be such that the catalase carrier does not inhibit any stage of germination or growth of microorganisms surviving the sterilization process.

Therefore, the catalase tablet 20 must not be metabolized by the surviving microorganisms and must not change the liquid consistency and composition of the growth promoting media. The catalase tablets 20 must disintegrate on contact with the media releasing catalase or other appropriate neutralizer into the immediate microenvironment of the (SCBI) for the purpose of decomposing hydrogen peroxide residue.

The preferred choice of the carrier for catalase delivery to the (SCBI) is finely powdered cellulose or corn starch. However, any natural or artificial carrier material can be used in the tablet 20 as long as it complies with the conditions specified hereinabove.

The inclusion of lyophilized catalase in the tablet 20 will prolong its enzymatic potency to provide an acceptable shelf life without freezing or refrigeration.

After activation the (SCBI) is placed in a conventional incubator at a temperature and for a time suitable for growing the microorganism in the growth promoting medium.

It is known in the art to utilize a so-called detector contained in the growth media which is capable of undergoing a visible change in color in response to the growth of a particular microorganism. The metabolites produced by a particular microorganism are designed to react with a given detector to produce a color change indicating that sterilization was not complete. The absence of a color change confirms that sterilization conditions were achieved.

Since such visible detectors in a culture medium are well known to those skilled in the art, further detailed discussion of the same is not deemed necessary.

Figure 7:
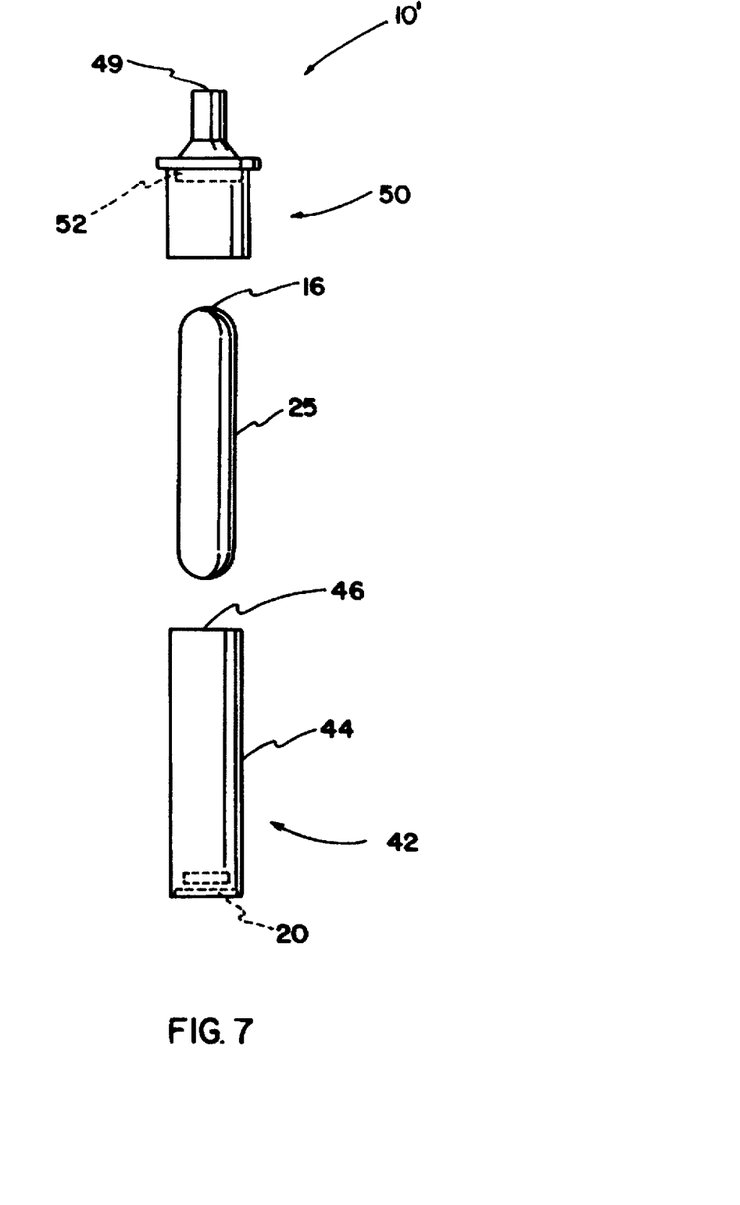
FIG. 7 is an exploded view of an alternative embodiment of the (SCBI) showing the components thereof.

Turning now to FIG. 7 there is shown therein an alternative embodiment of the (SCBI) of the present invention indicated generally at 10'. In this embodiment a translucent outer container, indicated generally at 42, has gas/liquid impermeable walls 44 and an open end 46.

This embodiment of the (SCBI) includes the same ampule 25 of growth promoting media including the same paper strip or sporedot 26 inoculated with a predetermined amount of microorganisms as described hereinabove.

Similarly, this embodiment utilizes a tablet 20 comprised of a hydrogen peroxide neutralizing composition such as catalase as previously described hereinabove.

Figure 8:
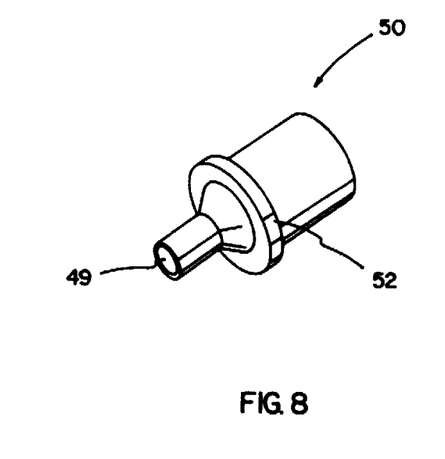
FIG. 8 is a perspective view of a vented cap which forms a part of the alternative embodiment of the (SCBI) illustrated in FIG. 7.

In this alternative embodiment the (SCBI) 10' includes a vented cap, indicated generally at 50, as more clearly shown in FIG. 8.

Cap 50 is secured over the open end 46 of the outer container 42 in its functional position and includes a central opening 49 which communicates with the interior of the container 42 to permit the flow of sterilant vapor therein during the sterilization cycle.

Cap 50 is provided with a closure barrier 52 which is secured on an inner surface thereof adjacent the vent opening 49. Barrier 52 is a vapor-permeable, microorganism-impermeable nonwoven fabric of the type sold under the tradename Tyvek or any other suitable material for this purpose. During assembly of the (SCBI) 10', the barrier 52 is secured permanently in position by cap 50 when installed on the outer container 42.

In practical use, the (SCBI) 10' is positioned within the sterilization chamber along with the objects to be sterilized in the same manner as described hereinabove. During the sterilization cycle a portion of the hydrogen peroxide sterilant permeates through the opening 49 and into the outer container 42 where it acts on the microorganism impregnated strip 16.

After being subjected to a sterilization cycle, the (SCBI) 10' is activated by compressing the deformable outer container 42 releasing the growth promoting medium contained within ampule 25 and mixing the same with the catalase tablet 20 as described hereinabove.

In all other respects the (SCBI) 10' is processed in the same manner as that described hereinabove to evaluate the sterilization cycle.

Figure 9:
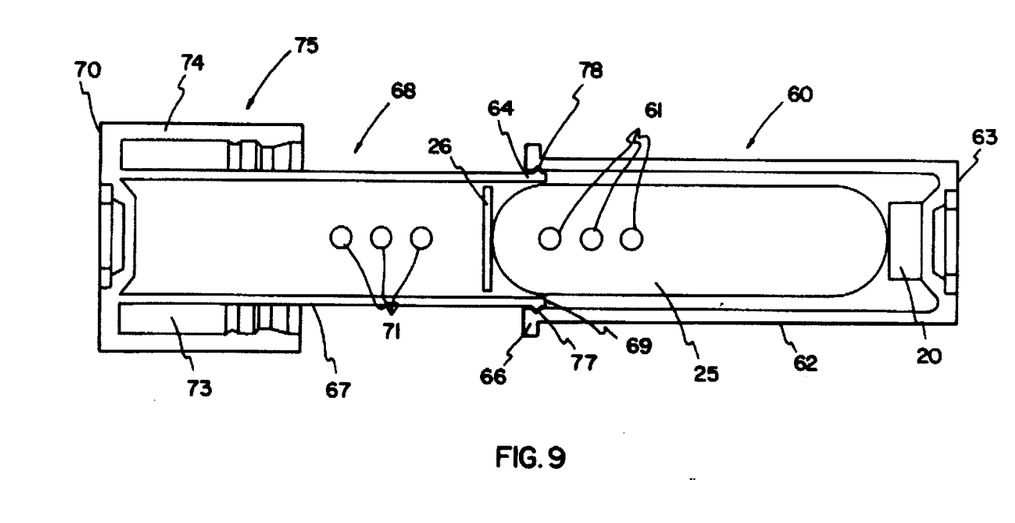
FIG. 9. is a cross-sectional view of an alternative embodiment of the (SCBI) shown in an unsealed sterilization test configuration.

Referring now to FIG. 9 there is shown therein yet another alternative embodiment of the (SCBI) of the present invention, indicated generally at 10". In this embodiment, a translucent outer tube, indicated generally at 60, has gas/liquid impermeable walls 62 with a plurality of openings 61 formed therein for permitting sterilizing agent penetration. The outer tube 60 includes a closed end 63 and an open end 64 into which a hydrogen peroxide neutralizing tablet 20 containing catalase has been deposited.

Outer tube 60 further includes a locking shoulder 66 that is integrally formed with the walls 62 of the outer tube in generally perpendicular relation thereto.

In this embodiment the outer tube 60 is fabricated from a flexible, translucent plastic material such as polypropylene or other suitable translucent material.

The outer tube 60 is configured and dimensioned to slidlingly receive an ampule 25 as described hereinabove containing a growth promoting medium.

In the embodiment shown in FIG. 9 the (SCBI) 10" includes an absorbent paper strip or sporedot 26 inoculated with a predetermined number of dormant microorganisms similar to that disclosed hereinabove.

The (SCBI) 10" includes an inner tube, indicated generally at 68, also having translucent, gas/liquid impermeable walls and having an open end 69 and a closed end 70.

The integrity of the walls 67 of inner tube 68 is similarly interrupted by the formation of a plurality of openings 71 which permit the flow of sterilizing agent to permeate to the inner surfaces of the vial 68 during sterilization.

The inner tube 68 is configured and dimensioned for telescoping engagement within the outer tube 60 prior to activation of the (SCBI) 10" as described hereinafter in further detail.

Still referring to FIG. 9 it can be seen that the (SCBI) 10" is provided with a molded cap, indicated generally at 75, which is integrally formed with the inner tube 68. Cap 75 includes generally cylindrical walls 74 which are radially disposed about the exterior surface of inner tube 68 so as to form a cylindrical groove 73 therebetween.

Figure 10:
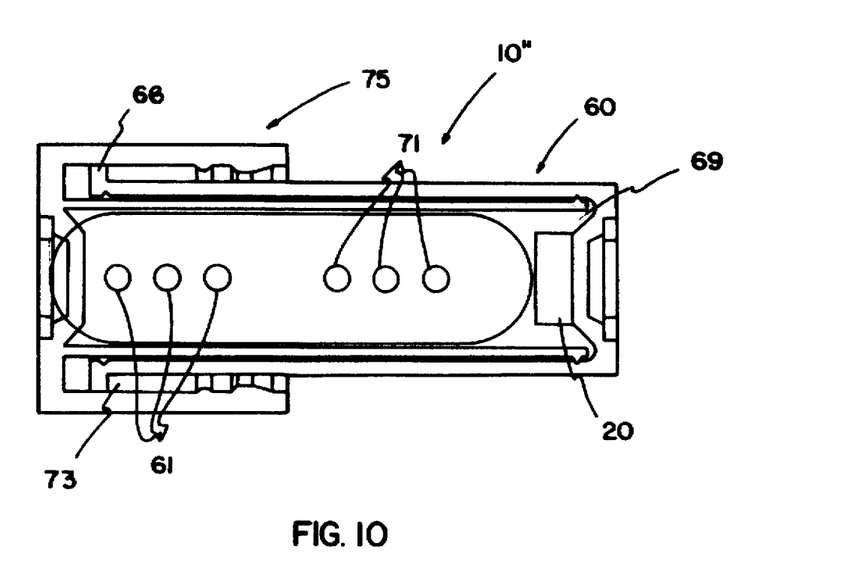
FIG. 10 is a cross-sectional view of the alternative embodiment of the (SCBI) of FIG. 9 shown in a sealed incubation configuration.

Groove 73 is configured and dimensioned so as to engage the locking shoulder 66 of outer vial 60 when (SCBI) 10" is sealed for incubation as shown in FIG. 10.

Prior to placing it within the chamber of the sterilizer along with the objects to be sterilized, the (SCBI) 10" is assembled to the unsealed sterilization test position shown in FIG. 9.

It will be noted that a distal end of the inner tube 68 is provided with a circumferential bead 77 being integrally formed about the outside diameter thereof which is adapted for engagement in a mating groove 78 integrally formed about the inside diameter of outer tube 60 adjacent the locking shoulder 66.

During the sterilization cycle the sterilant vapor permeates through the openings 61 and 71 to the interior of the outer tube 60 and the inner tube 68 where it acts on the microorganism inoculated sporedot 26 together with the contents and interior surfaces of the (SCBI) 10".

After being subjected to a sterilization cycle the inner tube 68 is inserted firmly into the outer tube 60 to the sealed incubation condition shown in FIG. 10 interlocking the shoulder 66 within the cap 75.

It will be appreciated by those skilled in the art that the ampule 25 is slightly longer than the internal space provided within the (SCBI) 10" in the sealed incubation condition shown in FIG. 10. Thus, pressure will be applied at the ends of the ampule when the cap 75 is interlocked with the outer tube 60. This pressure will cause the ampule 25 to break exposing the culture medium to the sporedot 26 and the catalase tablet 20.

It can be seen that in the sealed incubation position of FIG. 10, the openings 71 in the inner tube 68 are sealed by sliding engagement with the inner surfaces of wall 62. Similarly, the openings 61 formed in the outer tube 60 are sealed by the sliding engagement of the outer surface of wall 67 to provide a leak proof enclosure.

The efficacy of the sterilization cycle is directly related to the mass and penetration characteristics of the items to be sterilized. Otherwise stated, this means that not all of the items being sterilized in the chamber receive the same sterilant agent treatment. Thus, the size and shape of the articles to be sterilized may impair access of the sterilant agent to some parts of the load regardless of the means of sterilization.

To resolve this impaired access problem so-called test packs have been developed for the purpose of simulating the impaired access of the sterilization agent to partially hidden or enclosed surfaces of the items to be sterilized.

Thus, the test pack presents an additional challenge to the penetration characteristics of the sterilizing agent and creates the worst case scenario for evaluation purposes. Accordingly, when the microorganisms within the (SCBI) contained within a test pack have been eradicated, then all of the items exposed in the same chamber can be viewed as presumably sterilized with a high degree of confidence.

Thus, although the (SCBI) of the present invention can be used alone, it is generally desirable to incorporate the (SCBI) in a test pack.

Figure 11:
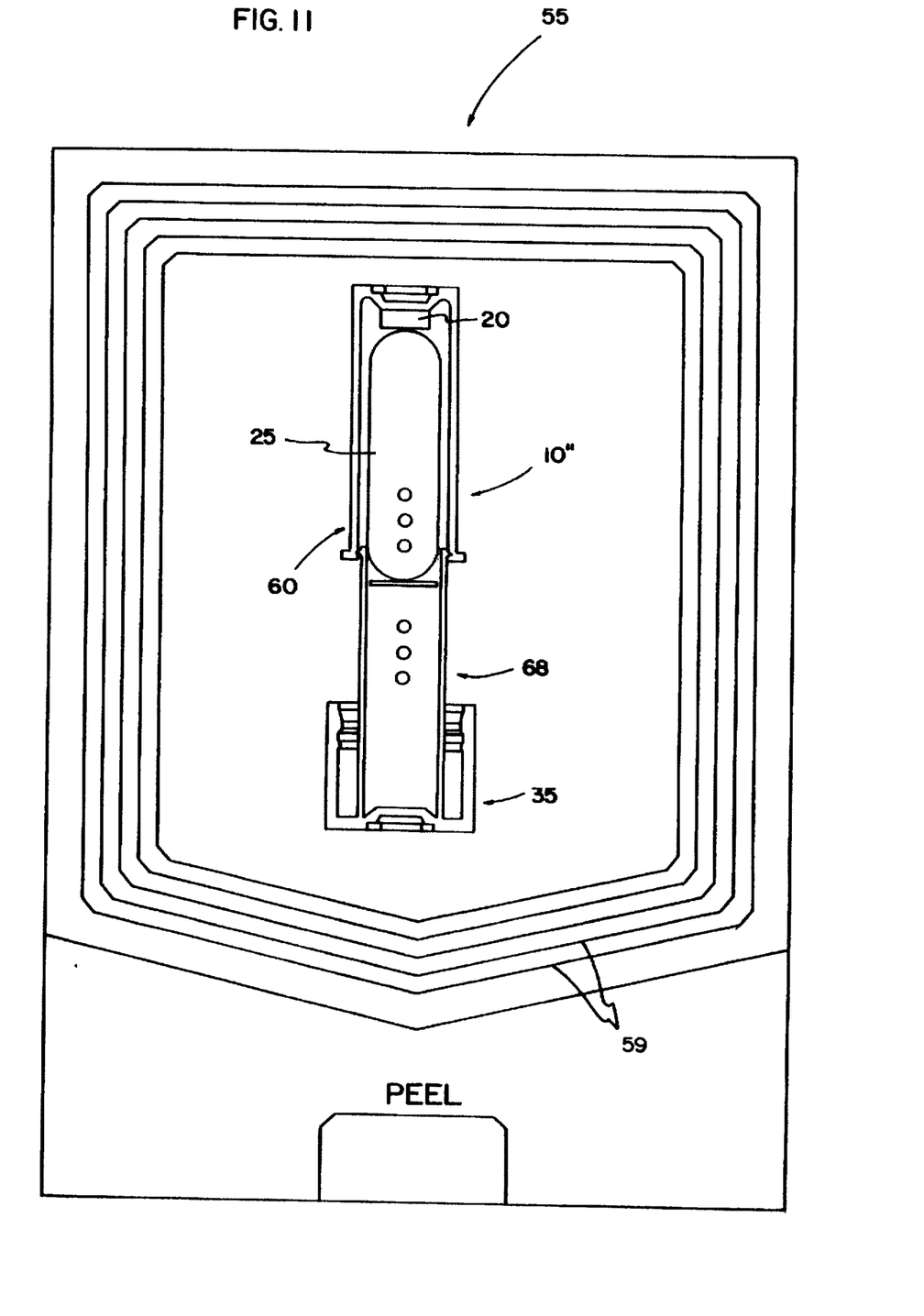
FIG. 11 is a top plan view of a test pack containing the alternative embodiment of the (SCBI) shown in FIG. 9 therein in an unsealed sterilization test configuration.

With reference to the drawings there is shown therein the improved (SCBI) of the present invention in a test pack, indicated generally at 55, as depicted in FIG. 11.

The test pack 55 includes a housing or pouch 56 which is fabricated from opposed sheets of a vapor-permeable, microorganism-impermeable material which are thermal sealed as at 59 creating an enclosure for the (SCBI) and a chemical indicator strip 58.

In the preferred embodiment pouch 56 is fabricated from a nonwoven fabric such as that sold under the trademark Tyvek or any other suitable material.

Indicator strip 58 is impregnated with a chemical which changes color when exposed to the hydrogen peroxide sterilant vapor.

In use, the test pack 55 containing the (SCBI) 10 is placed within the chamber of the sterilizer (not shown) along with the objects to be sterilized. During the sterilization cycle a portion of the sterilant vapor enters the gas permeable pouch 56.

As the sterilization cycle continues the sterilant permeates the pouch 56 and reaches that the indicator strip 58 causing a distinctive color transition indicating that it has been in contact with the sterilizing agent. The color transition of the indicator strip 58 results from exposure of an ink or other suitable chemical applied to the strip which reacts only on exposure to the selective means of sterilization and does not undergo color transition as a result of exposure to any other sterilization agent.

Alternatively, the test pack 55 may be provided with chemical indicator process ink (not shown) integrated into the test pack 55 itself to indicate passage through the appropriate sterilization cycle.

Since such chemical indicator strips and chemical indicator inks are well known to those skilled in the art, further detailed discussion of the same is not deemed necessary.

After being subjected to a sterilization cycle as part of the test pack 55, the activation of the (SCBI) 10" can be performed before or after retrieving it from the test pack. An examination of the chemical indicator strip 58 should be performed promptly after completion of the sterilization cycle, but before the test pack 55 is opened.

The test pack 55 is provided with a quick release mechanism wherein the thermal sealed layers are peeled apart to recover the (SCBI) in a known manner.

Post-exposure incubation of the activated (SCBI) is performed according to the manufacturer's instructions and recommendations.

From the above, it can be seen that the self-contained biological indicator (SCBI) of the present invention provides an accurate and reliable device for evaluating the efficacy of sterilization processes utilizing hydrogen and hydrogen peroxide/peracetic acid plasma and vapor as a sterilant.

The (SCBI) provides a vapor-permeable, microorganism impermeable container wherein an ampule containing growth promoting media, a paper strip or sporedot inoculated with dormant microorganisms, and a hydrogen peroxide neutralizing tablet can be readily mixed after exposure to the sterilization cycle to evaluate the efficacy of the sterilization process.

The (SCBI) of the present invention can be utilized by itself or in combination with a test pack to simulate the impaired access of sterilizing agent to the mass and penetration characteristics of the articles being sterilized in the sterilization chamber.

The terms "upper", "lower", "side", and so forth have been used herein merely for convenience to describe the present invention and its parts as oriented in the drawings. It is to be understood, however, that these terms are in no way limiting to the invention since such invention may obviously be disposed in different orientations when in use.

The present invention may, of course, be carried out in other specific ways than those herein set forth without departing from the spirit and essential characteristics of such invention. The present embodiments are, therefore, to be considered in all respects as illustrative and not restrictive, and all changes coming within the meaning and equivalency range of the appended claims are intended to be embraced therein.

What is claimed is:

1. A self-contained biological indicator for evaluating the effectiveness of a sterilizer utilizing hydrogen peroxide sterilant, said indicator comprising:

a deformable container means including a plurality of telescoping vial means adapted for sliding engagement one inside another from an unsealed sterilization test configuration to a sealed post-exposure configuration;

a source of viable microorganisms disposed within said container means;

a hydrogen peroxide neutralizing means capable of decomposing said sterilant and disposed within said container means; and a frangible ampule containing a culture medium capable of promoting growth of said microorganisms and including a detector means capable of reacting with the metabolites of said microorganisms to produce a visual indication of an incomplete sterilization cycle, said ampule being openable by pressure applied to an external surface of said container means to permit said medium, said microorganisms, and said neutralizing means to come into contact after exposure to a sterilization cycle such that said neutralizing means will decompose any residual hydrogen peroxide sterilant within said container means enabling any of said microorganisms surviving said sterilization cycle to grow in said medium to provide an indication of the effectiveness of said sterilizer.

2. The biological indicator of claim 1 wherein said source of microorganisms includes a paper strip inoculated with a predetermined concentration of said microorganisms.

3. The biological indicator of claim 2 wherein said paper strip is attached to an external surface of said ampule.

4. The biological indicator of claim 1 wherein said neutralizing means includes catalase in tablet form.

5. The biological indicator of claim 4 wherein said catalase tablet comprises a lyophilized powder mixed with a hygroscopic substance such as cellulose capable of disintegrating on contact with said medium.

6. The biological indicator of claim 1 wherein said vial means includes in inner vial and an outer vial being generally cylindrical in construction and adapted for sliding engagement one inside another, each of said vials further including a plurality of gas permeable openings therein to permit said sterilant to permeate said indicator during said sterilization cycle in said test configuration, said openings being sealable by said sliding engagement of said inner vial and said outer vial to said sealed post-exposure configuration.

7. The self contained biological indicator of claim 6 wherein said vial means further includes a gas/liquid impermeable cap means being adapted to receive said inner vial and said outer vial in said sealed post-exposure configuration, said cap means being configured and dimensioned to interlock with said inner vial and said outer vial to prevent unsealing thereof.

8. The biological indicator of claim 7 wherein said cap means is generally cylindrical in construction including at least one internal peripheral groove formed therein, said groove being adapted to interlock with a mating locking flange formed about the outer periphery of said outer vial to secure said cap means thereon.

9. The biological indicator of claim 8 wherein said cap means is integrally formed with said inner vial at one end thereof and adapted to interlock with said locking flange on said outer vial to secure said cap means to said outer vial.

10. The biological indicator of claim 1 wherein said vial means are fabricated from a translucent plastic material.

11. A method of evaluating the effectiveness of a hydrogen peroxide sterilizer by subjecting a self-contained biological indicator to a sterilization cycle, said indicator being of the type having a deformable container means including a plurality of telescoping vial means adapted for sliding engagement one inside another from an unsealed sterilization test configuration to a sealed post-test configuration, said indicator further including source of viable microorganisms, a hydrogen peroxide neutralizing means, and frangible ampule containing a culture medium for promoting growth of said microorganisms, said method comprising steps of:

providing said self-contained biological indicator;

setting said indicator in said unsealed sterilization configuration;

positioning said indicator in said sterilizer;

subjecting said indicator to a sterilization cycle;

engaging said vial means in said sealed post-test configuration;

activating said indicator by applying pressure to said deformable container means to permit said medium, said microorganisms, and said neutralizing means to come into contact; and incubating said indicator for a predetermined time to permit any of said microorganisms surviving said sterilization cycle to grow in said medium thereby providing an indication of the effectiveness of said sterilizer.

12. The method of claim 11 wherein the step of setting further includes the step of adjusting said vial means one inside another to expose a plurality of gas permeable openings formed therein to the atmosphere in said sterilizer allowing said sterilant to permeate said indicator.

13. The method of claim 12 wherein the step of positioning further includes inserting said indicator into a test pack comprising a gas permeable pouch means to simulate the mass and penetration characteristics of the items being sterilized.

* * * * *